(12) United States Patent
Edelman et al.

(10) Patent No.: US 9,091,617 B2
(45) Date of Patent: Jul. 28, 2015

(54) MECHANICAL TESTING SYSTEM AND METHOD

(75) Inventors: Elazer R. Edelman, Brookline, MA (US); Kay Dee Furman, Cambridge, MA (US); Gerard J. Desany, Beverly, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 376 days.

(21) Appl. No.: 13/695,343

(22) PCT Filed: May 31, 2011

(86) PCT No.: PCT/US2011/038581
§ 371 (c)(1),
(2), (4) Date: Oct. 30, 2012

(87) PCT Pub. No.: WO2011/150419
PCT Pub. Date: Dec. 1, 2011

(65) Prior Publication Data
US 2013/0042697 A1 Feb. 21, 2013

Related U.S. Application Data

(60) Provisional application No. 61/349,515, filed on May 28, 2010.

(51) Int. Cl.
*G01N 3/08* (2006.01)
(52) U.S. Cl.
CPC .......................................... *G01N 3/08* (2013.01)
(58) Field of Classification Search
CPC ....................................................... G01N 3/08
USPC ............................................................ 73/818
See application file for complete search history.

(56) References Cited

U.S. PATENT DOCUMENTS

| 2,448,133 | A | 8/1948 | Yorgiadis |
| 3,324,714 | A | 6/1967 | Simon et al. |

(Continued)

FOREIGN PATENT DOCUMENTS

| EP | 1201832 A1 | 2/2002 |
| WO | 2007042275 A1 | 4/2007 |
| WO | 2009157966 A1 | 12/2009 |

OTHER PUBLICATIONS

Search Report and Written Opinion of PCT/US2011/038581 dated Aug. 18, 2011.

*Primary Examiner* — Lisa Caputo
*Assistant Examiner* — Octavia Hollington
(74) *Attorney, Agent, or Firm* — Sutherland Asbill & Brennan LLP

(57) ABSTRACT

A fixture facilitates using a linear force of a uni-axial test machine to subject a test sample to bending forces. The test machine includes a frame and a crosshead. To generate the linear force, the crosshead translates with reference to the frame in a plane of motion. The fixture includes an upper connecting link, a lower connecting link, and two transverse arms. The upper connecting link is configured to attach to the crosshead for receiving the linear force, and the lower connecting link is configured to attach to the frame. The two transverse arms are pivotably carried between the upper and lower links. Each transverse arm has an inner end configured to attach to the test sample, the test sample being suspended between the arms. The transverse arms pivot in opposite directions in response to the linear force applied to the upper connecting link, exposing the sample to bending forces.

18 Claims, 5 Drawing Sheets

(56) References Cited

U.S. PATENT DOCUMENTS

| | | | |
|---|---|---|---|
| 4,594,900 A * | 6/1986 | Pellerin et al. | 73/806 |
| 5,231,882 A | 8/1993 | Bertele et al. | |
| 5,693,890 A * | 12/1997 | Holmes | 73/856 |
| 6,647,802 B2 * | 11/2003 | Wilson-Hackworth et al. | 73/826 |
| 2003/0192385 A1 | 10/2003 | Uhlik et al. | |
| 2004/0016301 A1 | 1/2004 | Moreno et al. | |
| 2013/0205911 A1 * | 8/2013 | Wang et al. | 73/812 |

\* cited by examiner

MECHANICAL TESTING SYSTEM AND METHOD

CROSS-REFERENCE TO RELATED APPLICATIONS

This application claims priority to U.S. Provisional Application Ser. No. 61/349,515, entitled "Systems and Methods for Multimodal Mechanical Testing of Medical Devices," filed May 28, 2010, which is incorporated herein by reference in its entirety. This application is a national phase entry of PCT patent application serial number PCT/US2011/038581 filed on May 31, 2011, designating the United States of America.

TECHNICAL FIELD

The present disclosure generally relates to mechanical testing systems and methods, and more particularly relates to mechanical testing systems and methods for medical devices.

BACKGROUND

Implantable medical devices are often exposed to a number of mechanical tests before being used in human patients. The mechanical tests expose test samples of the medical device to a variety of forces so that the mechanical integrity of the device can be investigated. For example, medical stents are often subjected to a battery of mechanical tests that assess the behavior of the medical stent in response to bending, compression, tension, and radial pulsation. The mechanical tests may assess whether the stent can sustain the maximum expected load, or cyclical loads of long-term use, without failing. Thereby, the safety and efficacy of the stent can be identified before the device is implanted in humans.

Many known mechanical testing systems are not suited for performing the range of mechanical tests to which a stent is normally subjected. For example, one known mechanical testing system is a uni-axial test machine, which features a crosshead that oscillates within a stationary frame. A test stent is mounted to the stationary frame, and as the crosshead moves up and down, a load is applied to the stent.

One problem with the uni-axial test machine is that it applies force in only one direction. The force is applied along a line of action that is parallel to the direction of travel or plane of motion of the crosshead. Thus, the uni-axial test machine is suited for testing modes that require the application of a uni-axial force to the test stent, such as compression and tension tests, but not for other testing modes that require the application of different forces in different directions.

To adapt the uni-axial test machine for other tests, a fixture may be employed. One known fixture adapts the uni-axial test machine for bending tests. The fixture includes two supports for supporting the test sample within the stationary frame. The fixture is placed in the stationary frame, and the test sample is rested on the fixture suspended between the supports. The uni-axial machine then applies a linear force to the test sample about its mid-point, causing the test sample to bend. Because the bending force is applied to one point of the test sample, and each of the two supports exert a return force on the test sample, such a bending mode is known as "three-point bending".

Testing modeled on three-point bending may not realistically mimic the manner in which a stent experiences bending within the body. Forces are not usually applied within the body to a single point of application. Additionally, forces are not usually applied within the body in a perpendicular direction. Because the three-point bending test applies force in an unnatural manner, the bending that the test stent experiences may be misleading. The mid-point of the stent, which is directly contacted with the load, may experience unreasonably high compression or deformation. Conversely, the end points of the stent, which are not directly contacted with the load, may experience relatively little or no bending, as the load may not be uniformly transferred along the length of the stent.

Despite these issues, testing modeled on three-point bending is often employed because the uni-axial test machine is readily available. Such a machine is standard equipment in many testing laboratories. The stent is then subjected to other testing modes separately. The separate application of other test modes does not adequately mimic the conditions in the body, where the stent may experience bending in combination with tension, compression, torsion, or radial pulsation.

From the above, a need exists for mechanical testing systems and methods that can subject a medical device such as a stent to realistic bending forces. It may be desirable if the systems and methods are suited for use with a conventional uni-axial test machine, which is available in many lab environments. If also may be desirable if the systems and methods are suited for subjecting the medical device to one or more additional testing modes simultaneously with bending.

SUMMARY

In one embodiment, a fixture is provided for a uni-axial test machine. The fixture facilitates using a linear force of the uni-axial test machine to subject a test sample to bending forces. The uni-axial test machine includes a frame and a crosshead. The crosshead translates with reference to the frame in a plane of motion to generate the linear force. The fixture includes an upper connecting link, a lower connecting link, and two transverse arms. The upper connecting link is configured to attach to the crosshead of the uni-axial test machine for receiving the linear force. The lower connecting link is configured to attach to the frame of the uni-axial test machine. The two transverse arms are pivotably carried between the upper and lower links. Each transverse arm has an inner end that is configured to attach to the test sample so that the test sample is suspended between the arms. The transverse arms are operable to pivot in opposite directions in response to the linear force applied to the upper connecting link, exposing the test sample to bending forces.

The upper link, the lower link, and the transverse arras lay in the plane of motion of the uni-axial test machine. The fixture also may include a guide plate. The guide plate lays in a plane that is parallel to but spaced apart from the plane of motion, the guide plate having two guide slots. The transverse arms are movably guided along the guide slots to control a distance between the inner ends of the transverse arms. The guide slots may constrain the motion of the transverse arms to the plane of motion of the uni-axial test machine.

The guide plate may be substituted with another guide plate having different guide slots, which cause the inner ends of the transverse arms to be closer together or farther apart. Alternatively, the guide plate may be adjusted to adjust the spacing of the guide slots, causing the inner ends of the transverse arms to be closer together or farther apart. Moving the inner ends of the transverse arms closer together or farther apart exposes the test sample to compressive or tensile forces as the transverse arms pivot.

In some embodiments, the upper link has two downwardly extending upper prongs, including a left upper prong and a right upper prong. Each upper prong is associated with an upper roller, the left upper prong associated with a left upper roller and the right upper prong associated with a right upper roller. Similarly, the lower link has two upwardly extending lower prongs, including a left lower prong and a right lower prong. Each lower prong is associated with a lower roller, the left lower prong associated with a left lower roller and the right lower prong associated with a right lower roller. Each of the transverse arms is pivotably carried between the upper and lower links on one of the upper rollers and one of the lower rollers, a left transverse arm carried on the left upper roller and the left lower roller, and a right transverse arm carried on the right upper roller and the right lower roller.

In some embodiments, at least one of the transverse arms is associated with a gear system operable to apply a torsional force to the test sample.

In some embodiments, the fixture includes an enclosure that creates a closed fluid path between the transverse arms. Each of the transverse arms comprises an inner channel for providing fluid to or returning fluid from the enclosure.

In another embodiment, a test system includes a frame, a crosshead, a lower link, an upper link, and two arms. The crosshead is operable to translate up and down within the frame. The lower link is fixably mounted to the frame. The upper link is fixably mounted to the crosshead. The two arms that are pivotably mounted between the upper and lower links. The arms are operable to pivot in opposite directions in response to translation of the crosshead.

The test system also may include a guide plate. The guide plate has two guide slots, and the arms are movably guided along the guide slots to control a distance between ends of the arms. The guide plate can be adjusted or substituted to change the configuration of the guide slots, changing the distance between the ends of the arms.

In some embodiments, a closed fluid path is formed between the two arms. The closed fluid path is in fluid communication with a pump that is operable to direct fluid through the closed fluid path in a pulsatile manner.

In another embodiment a method can use a linear force to expose a test sample to bending forces. The method includes attaching the test sample to two pivot anus such that the test sample is suspended between the arms and transferring a linear force onto each of the pivot arms such that the arms pivot in opposite directions. Thereby, the test, sample is exposed to bending forces.

A distance between ends of the arms can be controlled to control the application of compressive or tensile forces to the test sample. The distance between ends of the arms also can be varied to vary the application of compressive or tensile forces to the test sample. A range of pivot of the arms can be controlled to control a maximum bending angle to which the test sample is exposed. The direction of the linear force can be reversed to subject the test sample to fatigue testing. The shaft extending from an end of at least one of the arms can be rotated to expose the test sample to a torsional force, with the shaft rotating about an axis of rotation that is generally coincident with a longitudinal axis of the at least one arm. Fluid can be flowed along a closed fluid path between the arms in a pulsatile manner to expose the test sample to radially pulsating forces.

In some embodiments, the linear force is transferred to the pivot arms through a connecting link. The connecting link includes an upper connector and two lower prongs. The lower prongs are spaced apart from each other in a symmetrical manner with reference to the upper connector. Each of the lower prongs is associated with one of the pivot arms. The upper connector receives the linear force, and each lower prong transfers a portion of the linear force onto one of the pivot arms. The ends of the pivot arms may be constrained in guide slots, such that application of the portion of the linear force to the pivot arms causes the ends of the arms to travel along the guide slots. The test sample may be a medical stent or another implantable medical device.

Other systems, devices, methods, features, and advantages of the disclosed mechanical testing systems and methods will be apparent or will become apparent to one of skill in the art upon examination of the following figures and detailed description. All such additional systems, devices, methods, features, and advantages are intended to be included within the description and are intended to be protected by the accompanying claims.

BRIEF DESCRIPTION OF THE FIGURES

The present disclosure may be better understood with reference to the following figures. Matching reference numerals designate corresponding parts throughout the figures, and components in the figures are not necessarily to scale.

DETAILED DESCRIPTION

Described below are embodiments of mechanical testing systems and methods for medical devices. The systems and methods can be employed to test the mechanical integrity of a medical device such as a stent or a prosthetic heart valve. The systems and methods may expose the medical device to bending forces, either alone or in combination with compressive forces, tensile forces, torsional forces, radial pulsation forces, or combinations thereof. Unlike existing testing systems and methods that apply a bending load directly to a central portion of the medical device, such as its mid-point, the present systems and methods apply the bending forces to end portions of the medical device, permitting a more uniform transfer of the bending load along the length of the medical device. Thus, the medical device advantageously can be tested under bending loads that are more consistent with the loads experienced inside of the human body.

In one embodiment, a mechanical testing system includes a uni-axial test machine and a fixture positioned in the uni-axial test machine. The medical device is associated with the fixture. The uni-axial test machine applies a linear force to the fixture, and the fixture transfers the force to end points of the medical device, causing the medical device to bend. The bending mode is comparable to "four-point bending", as the two end portions of the medical device each experience a bending force and respond with a return force. Such bending more accurately mimics the conditions to which medical devices are exposed in the body.

The systems and methods described herein can be used to mechanically test a medical device, such as a cardiac stent, a peripheral cardiovascular stent, a cardiac valve, a cardiovascular percutaneous valve, a pulmonary stent, or a urinary stent, among others. The systems and methods may be particularly suited for elongated cage-like devices, which have a partially open structure. The tested device is generally described as being a stent within the present disclosure for the purposes of simplicity, although the systems and methods can test any suitable test sample, including samples that are medical devices other than stents and samples that are not medical devices.

Figure 1:
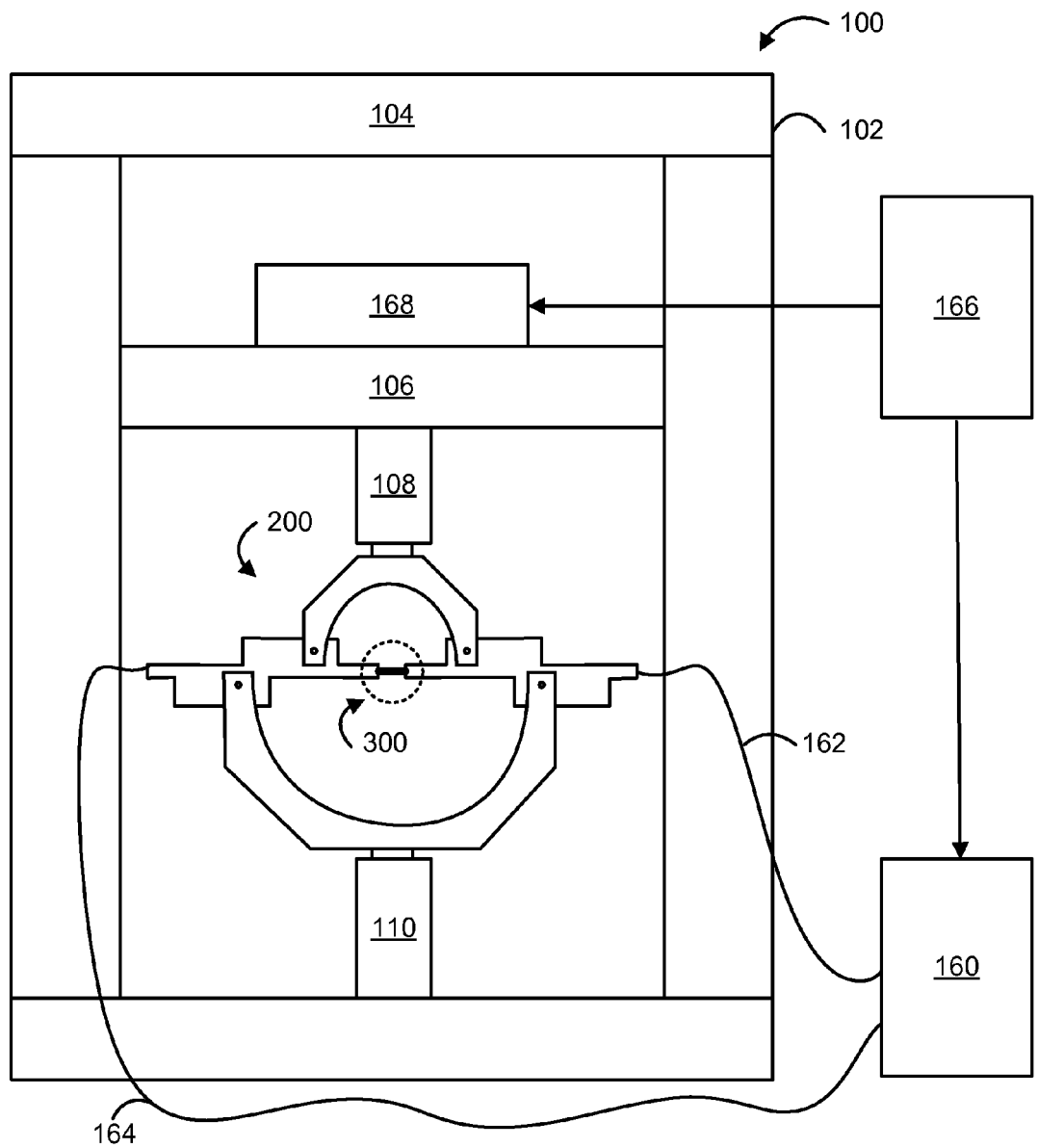
FIG. 1 is a schematic plan view of an embodiment of a mechanical testing system.

An embodiment of a mechanical testing system 100 is shown in FIG. 1. The testing system 100 generally includes a uni-axial test machine 102 associated with a four-point bending fixture 200. The fixture 200 is adapted to expose a test sample 300 associated with the fixture 200 to four-point bending. The fixture 200 has a connecting link that pivotably carries two arms. The connecting link can attach to the uni-axial test machine 102, and the two arms can attach to the test sample, the test sample suspended between inner ends of the arms, which are facing or adjacent to each other when the arms in horizontally positioned. When the connecting link receives a linear force from the uni-axial test machine 102, the connecting link applies a rotation force to each of the two arms, causing the anus to pivot. The arms are symmetrically mounted so that their inner ends to pivot in opposite directions, meaning that one arm pivots in a clockwise direction when the other arm pivots in a counterclockwise direction. When the connecting link is pushed downward by the machine 102, the arms pivot downward. When the connecting link is pulled upward by the machine 102, the arms pivot upward. The pivot of the arms exposes the test sample positioned between the arms to four-point bending.

In the illustrated embodiment, the uni-axial test machine 102 has a stationary frame 104 and a movable crosshead 106. The stationary frame 104 includes two vertical side supports and upper aid lower connecting supports. The movable crosshead 106 is positioned between the vertical side supports and can ride along the side supports in a vertical direction, along a plane of motion that is parallel to the plane of the paper. The machine 102 also includes a movable upper adapter 108 attached to the crosshead 106 and a stationary lower adapter 110 attached to the lower connecting support. The upper and lower adapters 108, 110 are conventionally used to attach a test sample to the machine 102, but within the present disclosure, the upper and lower adapters 108, 110 are used to attach the fixture 200 to the machine 102. An actuator causes the crosshead 106 to translate upward and downward along its plane of motion, applying a linear force to the fixture 200. However, tire urn-axial test machine 102 may have a range of other configurations within the scope of the present disclosure. For example, the stationary frame may be a single column on which the crosshead rides.

Figure 2:
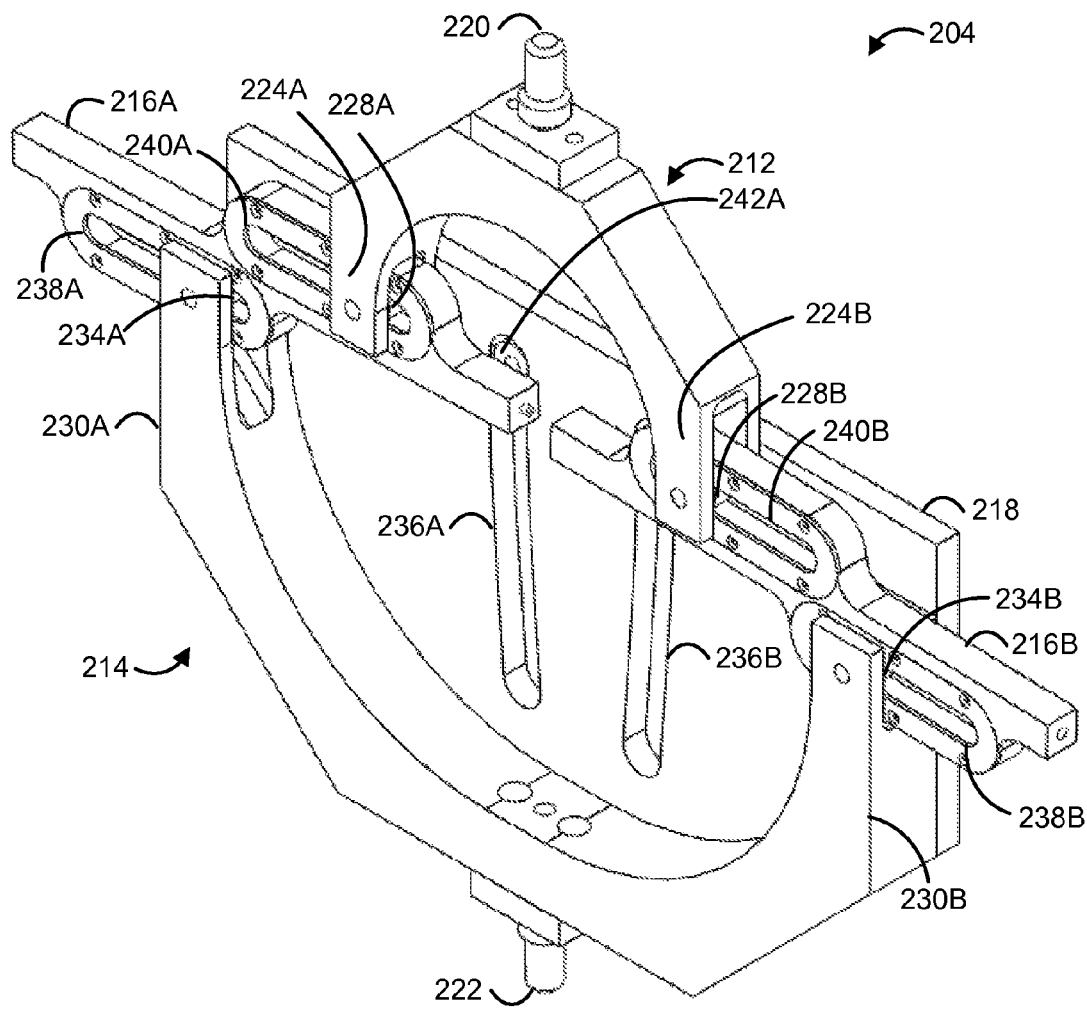
FIG. 2 is a perspective view of an embodiment of a four-point bending fixture for use with the embodiment of a mechanical testing system shown in FIG. 1.

FIG. 2 is a perspective view illustrating the fixture 200 in further detail. As shown, the fixture 200 includes an upper link 212, a lower link 214, a left transverse arm 216A, a right transverse arm 216B, and a guide plate 218. The fixture 200 can be attached to the uni-axial test machine 102 via the upper and lower links 212, 214. For example, the upper link 212 may have an upper connector 220 that attaches to the movable upper adapter 108 of the uni-axial test machine 102, and the lower link 214 may have a lower connector 222 that attaches to the stationary lower adapter 110 of the uni-axial test machine 102. The connectors 220, 222 may be threaded projections in embodiments in which the adapters 108, 110 have threaded openings, although other connection means may be used, whether now-known or later developed.

With reference back to FIG. 1, when the fixture 200 is attached to the uni-axial test machine 102, the links 212, 214 lie in the plane of motion of the uni-axial test machine 102. The upper link 212 translates in the plane of motion with movement of the crosshead 106, while the lower link 214 remains stationary.

In the illustrated embodiment the upper link 212 has left and right prongs 224A, 224B that extend along the plane of motion. The prongs 224 extend away from the connector 220 toward a center of the fixture 200 and outward from the connector 220 toward sides of the fixture 200. Thus, the prongs 224 have end portions that are horizontally spaced apart from each other. Each end portion supports a roller 228 that is mounted on an axis of rotation. The axis of rotation is perpendicular to the plane of motion of the test machine 102 when the fixture 200 is mounted therein.

Similarly, the lower link 214 has left and right prongs 230A, 230B that extend along the plane of motion of the test machine 102. The prongs 230 extend away from the connector 222 toward a center of the fixture 200 and outward from the connector 222 toward sides of the fixture 200. Thus, the prongs 230 have end portions that are horizontally spaced apart from each other. Each end portion supports a roller 234 that is mounted on air axis of rotation. The axis of rotation is perpendicular to the plane of motion of the test machine 102.

In the illustrated embodiment, the lower link 214 is relatively larger than the upper link 212. Its prongs 230 are relatively longer than the prongs 224 and define a larger space therebetween. However, other configurations are possible.

The guide plate 218 also is generally planar and is mounted behind the upper and lower links 212, 214 in a plane that is parallel to but spaced apart from the plane of motion of the test machine 102. In the illustrated embodiment, the guide plate 218 is mounted to the lower link 214 and is therefore stationary, although other configurations are possible.

The guide plate 218 has left and right guide slots 236A, 236B formed through at least a portion of its surface. The guide slots 236 traverse a substantial portion of the fixture 200 in a vertical direction, although the guide slots 236 have a slight curvature or bend in a horizontal direction. In some embodiments, such as the one shown in FIGS. 4-5, the guide slots 236 curve in one direction, but in other embodiments, such as the one shown in FIGS. 6-8, the guide slots 236 curve in two directions. The shape of the guide slots 236 is described in further detail below.

The arms 216 are movably supported between the upper and lower links 212, 214. The left arm 216A is supported between the left prongs 224A, 230A of the upper and lower links 212, 214, while the right arm 216B is supported between the right prongs 224B, 230B of the upper and lower links 212, 214. More particularly, the left arm 216A includes an outer transverse slot 238A that is mounted about the left roller 234A on the lower link 214 and an inner transverse slot 240A that is mounted about the left roller 228A on the upper link 212. Additionally, the left arm 216A has a roller 242A mounted on its inner end portion that rides in the left guide slot 236A of the guide plate 218. Like the rollers on the prongs, the roller 242A on the left arm 216A is mounted on an axis of rotation that is perpendicular to the plane of motion of the test machine 102.

Similarly, the right arm 216B includes an outer transverse slot 238B that is mounted about the right roller 234B on the lower link 214 and an inner transverse slot 240B that is mounted about the right roller 228B on the upper link 212. Additionally, the right arm 216B has a roller (not visible in FIG. 2) mounted on its inner end portion that rides in the right guide slot 236B of the guide plate 218. The roller on the right arm 216B is mounted on an axis of rotation that, is perpendicular to the plane of motion of the test machine 102.

The left and rights arms 216A, 216B are positioned on the links 212, 214 so that their inner ends are facing or adjacent to each other with a gap or space formed therebetween. The test sample is positioned in tire gap and is mounted to tire inner ends of the arms 216, such that the test sample extends between the arms 216. In particular, one end of the test sample is mounted to the inner end of the left arm 216A, and the other end of the test sample is mounted to the inner end of the right arm 216B. The test sample can be mounted to the arms 216 in a variety of ways, one example of which is shown in FIG. 3.

Figure 3:
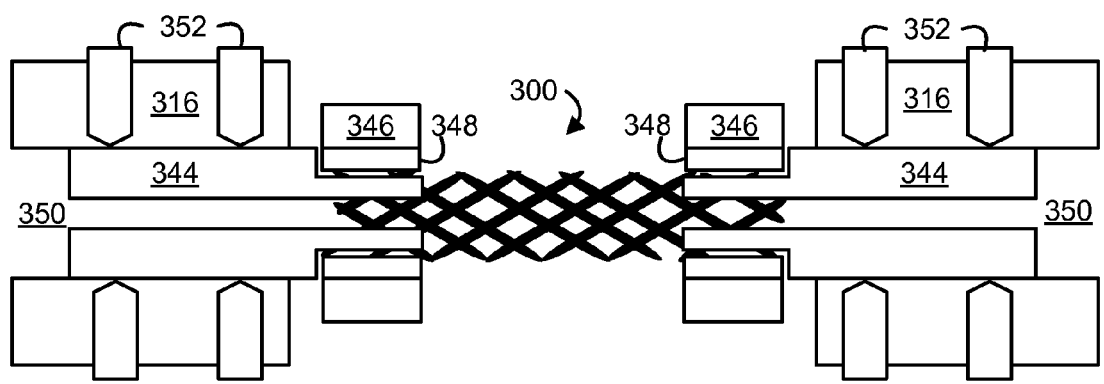
FIG. 3 is a cross-sectional plan view of a stent attached to arms of a four-point bending fixture with sample holders.

In particular, FIG. 3 is a cross-sectional plan view of a test sample 300 mounted in a gap between two arms 316 using sample holders 344. The test sample 300 has a hollow cylindrical interior. To attach the test sample 300 to one of the arm 316, the test sample 300 is attached to the sample holder 344, and the sample holder 344 is attached to the arm 316. On one end, the sample holder 344 has an outer diameter that is slightly smaller than an inner diameter of the test sample 300, so that the sample holder 344 can be inserted into the test sample 300. Tire sample holder 344 is then attached to the test sample 300 using a fastener 346, such as a snapper hose clamp. Optionally, a sleeve 348 formed from a complaint material, such as vinyl or urethane, may be positioned between the test sample 300 and the fastener 346 to provide cushion. On the other end, the sample holder 344 has an outer diameter that is slightly smaller than an inner diameter of a channel 352 defined within the arm 316, so that the sample holder 344 can be inserted into the arm 316. The sample holder 344 is then attached to the arm 316 using a fastener 352, such as a number of set screws. In the illustrated embodiment, the sample holder 344 defines a hollow interior channel that permits fluid to flow there through, as described in further detail below, although the interior channel may be omitted.

The left end of the test sample 300 can be attached to the inner end of the left arm 316 with one sample holder 344, and the right end of the test sample 300 can be attached to the inner end of the right arm 316 with another sample 344. Thereby, the test sample 300 is mounted between the arms 316, with its middle portion suspended and its end portions attached to the arms 316.

The sample holders 344 facilitate securely and quickly attaching the test sample 300 to the arms 316. Test samples 300 having different shapes and configurations can be attached to the arms 316 by varying the configuration of the sample holders 344. For example, sample holders 344 with various outer diameters can be used to accommodate stents of various sizes. The sample holders 344 also facilitate quickly changing the test sample 300 while preserving the sensitivity of the load measurement. However, the sample holders 344 may be omitted, in which case the test sample 300 may be attached directly to the arms 316 in other manners.

With reference back to FIG. 1, the operation of the system 100 is described below. The test sample 300 is subject to bending by operating the uni-axial test machine 102. The actuator causes the crosshead 106 to translate in the plane of motion (i.e., the plane of the paper), applying a linear force to the fixture 200 that causes its arms to rotate downward or upward, bending the sample suspended therebetween.

The operation of the system 100 is further described with reference to FIGS. 4 and 5, which are plan views of the fixture 200 illustrating the fixture 200 in motion. When the uni-axial test machine 102 applies a downward linear force on the upper link 212, the upper link 212 translates downward in the plane of motion, while the lower link 214 remains stationary. The downward translation of the upper link 212 is transferred to its prongs, effectively splitting the downward linear force into two downward linear forces that are parallel but spaced apart from each other in the plane of motion. The left prong applies a downward linear force on the left arm 216A about its inner transverse slot, and the right prong applies a downward linear force on the right arm 216B about its inner transverse slot. Because the end portions of the arms 216 are constrained in the guide slots 236 of the guide plate 318, the arms 216 respond to the two parallel downward linear forces by pivoting in the plane of motion, the left arm rotating in a clockwise direction, and the right arm rotating in a counterclockwise direction. The end portion of each arm 216 travels along the corresponding guide slot 236 in the guide plate 218 via the guide slot roller, and the remainder of the arm 216 travels about the arms rollers within the transverse slots.

Figure 4:
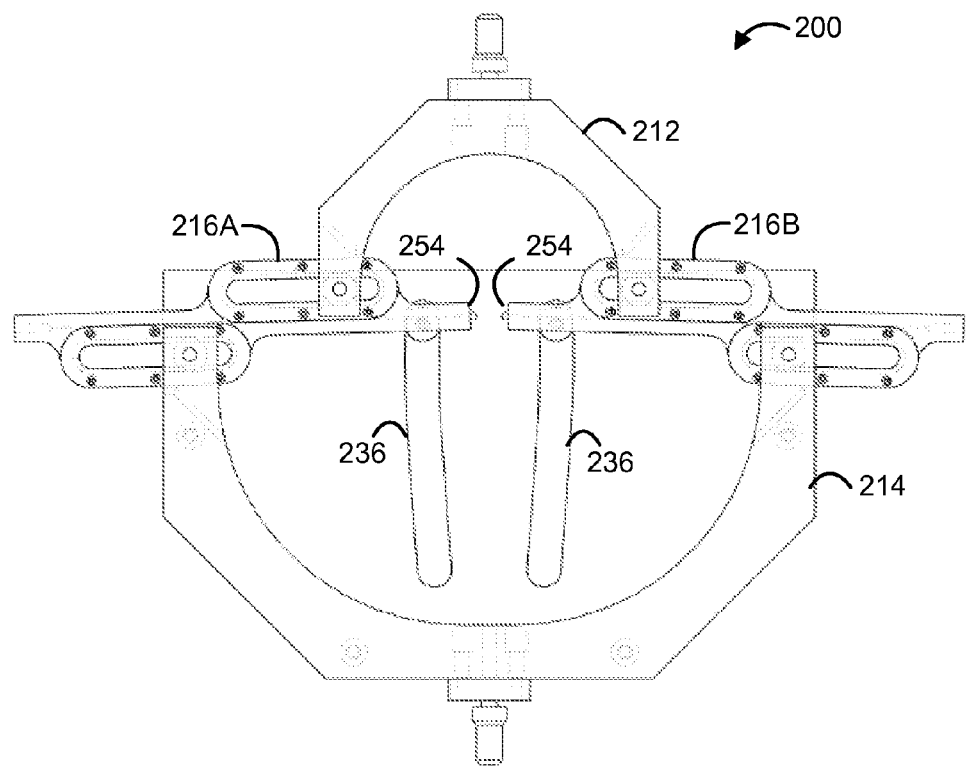
FIG. 4 is a plan view of the four-point bending fixture shown in FIG. 2, illustrating the fixture with its arms in a horizontal position.
Figure 5:
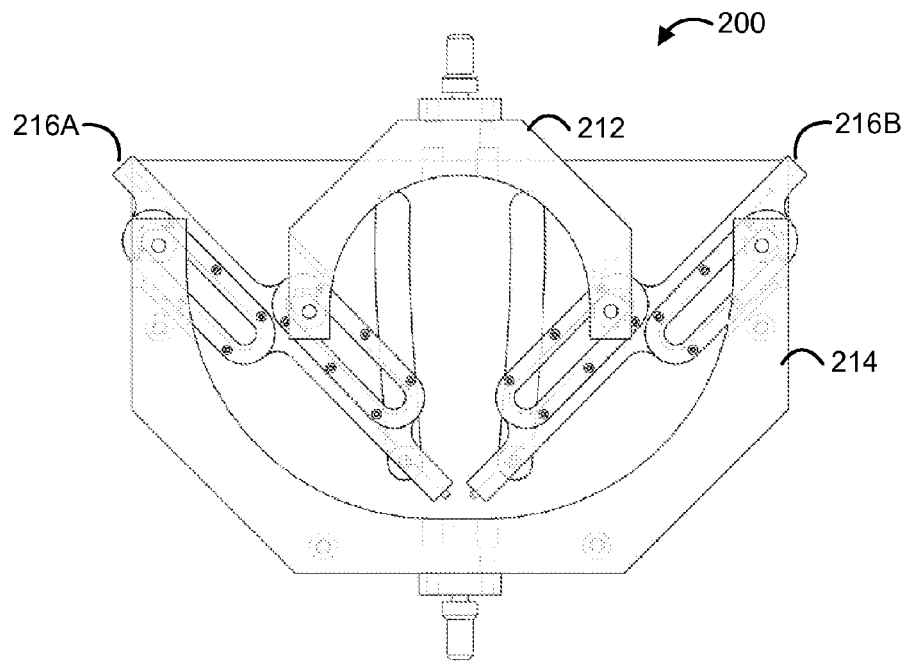
FIG. 5 is a plan view of the four-point bending fixture shown in FIG. 2, illustrating the fixture with its arms in a pivoted position.

Thereby, a test sample suspended between the inner ends of the arms 216 is exposed to bending, as evidenced by the orientation of the inner end surfaces 254 of the arms 216 in FIG. 4 and FIG. 5. In FIG. 4, the arms 216 are in a horizontal position, such that the inner end surfaces 254 of the arms 216 are parallel to each other. When the arms 216 are in the horizontal position, tire test sample is not exposed to any bending forces. In FIG. 5, the arms 216 are in a downward pivoted position, such that the inner end surfaces 254 of the arms 216 are angled with reference to each other. When the arms 216 are in the downward pivoted position, the test sample is exposed to bending forces. The left arm 216A applies a downward force to the left end of the test sample, the right arm 216B applies a downward force to the right end of the test sample, and the test sample exerts return force on the arms 216, resulting in four-point bending.

The direction of the applied linear forces may be reversed to return the arms 216 to the horizontal position, thereby removing the bending forces from the test sample. When the uni-axial test machine 102 applies an upward linear force on the upper link 212, the upper link 212 translates upward while the lower link 214 remains stationary. The prongs apply parallel but spaced apart upward linear forces on the arms 216, causing the arms to pivot in the plane of motion, the left arm rotating in a counterclockwise direction, and the right arm rotating in a clockwise direction. Thereby, the arms 216 are returned to the horizontal or rest position, and the bending forces are removed from the test sample.

The downward and upward linear forces can be applied in an alternating fashion to oscillate the arms 216 between the horizontal and pivoted positions, subjecting the test sample to bending fatigue testing.

In embodiments in which the test sample is associated with the arms 216 via sample holders, the load is transferred to the test sample through the sample holders. The sample holders may facilitate a smooth transfer of the load to the sample. The amount of interaction between the test sample and the sample holder can be controlled to distribute the bending load onto the test sample. The compliant sleeve, if present, also facilitates distributing the load and may reduce the likelihood of the test sample slipping about the sample holder.

The fixture 200 facilitates exposing the test sample to a bending mode that more accurately reflects bending conditions within the human body, such as the bending conditions experienced by a cardiovascular stent in an artery. By applying the bending load to both ends of the test sample, the bending load may be transferred along a greater portion of the length of the test sample, facilitating more realistic bending. In some cases, the test sample experiences relatively uniform bending along all or most of its length. Applying the bending forces to the end portions of the test sample also reduces compression or deformation of the test sample at the point of application of the bending force. The sample holders may further reduce compression and deformation by applying the bending load over the outer surface of an end portion of the test sample, such as using a sample holder. The motion of the arms about the rollers may be smooth and stable, facilitating better weight support and smoother force transfer for more uniform bending. The bending also may be relatively balanced due to the symmetrical configuration of the fixture about the line of action of uni-axial test machine. For example, the prongs, arms, and slots may be symmetrically positioned with reference to the line of action of the uni-axial text machine. The bending also may be relatively balanced as the motion of the fixture may be confined to a single plane of action.

It should be noted that the fixture 200 is merely one example of a fixture that can be employed in the test system 102. In other embodiments, the fixture may have other configurations. For example, the configuration of the fixture could be simplified, such as by reducing the number of slots in the arms, by reducing the number of rollers, or by removing the guide plate.

The fixture also may have other configurations to expose the test sample to alternative bending modes, either alone or in combination with compression and tension. In particular, the bending mode can be varied by changing the guide slots in the guide plate. In some embodiments, the guide plate can be changed by removing a fixture with one guide plate from system and attaching a fixture with another guide plate to the system, in other embodiments, the guide plate may be removably associated with the fixture, such that the guide plate can be changed by removing the guide plate from the fixture and attaching another guide plate to the fixture. In still other embodiments, the guide plate may be mounted to the system separately from the remainder of the fixture, such that the guide plate can be changed by removing the guide plate from the system and attaching another guide plate to the system. Other variations also are possible.

The relative position and shape of the guide slots in the guide plate determines whether the test sample is exposed to bending alone or in combination with compression or tension. Additionally, the shape of the guide slots determines whether the test sample is exposed to bending in one direction and in two directions. The shape of the guide slots also determines the maximum angle of bending.

Pure bending without tension or compression is accomplished with guide slots that are shaped and positioned so that the distance between the inner end surfaces of the arms is fixed and does not change as the arms traverse the length of the guide slot. Compression or tension superimposed with bending is accomplished with guide slots that are inwardly or outwardly positioned from the pure bending configuration. For example, the guide slots can be closer together to subject the test sample to bending and compression, or the guide slots can be farther apart to subject the test sample to bending and tension. Of course, the actual position of the guide slots that achieve pure bending, bending with compression, and bending with tension varies depending on, for example, the length of the sample and the distance between the sample and the inner end surfaces of the arms.

The guide slots also may be shaped so that the relative position between the end surfaces of the arms varies as the arms traverse the length of the guide slot, so that, the test sample is exposed to bending in combination with variable compression, or tension. For example, the shape and position of the guide slots may be selected to vary the presence or compression or tension as the arms travel the length of the guide slot. The shape and position of the guide slots also may be selected to vary the extent of the compression or tension as the arms travel, the length of the guide slots. The guide slots also may be configured to expose the test sample to both tension and compression in an alternating manner.

The shape of the guide slots also can be varied to achieve uni-directional or bi-directional bending. For example, the guide slots may curve in only one direction to achieve bending in one direction only, or the guide slots may curve in two directions to achieve bending it both directions, such as fully reversed bending. Additionally, the shape of the guide slots may determine the maximum angle of bending to which the test sample is subjected.

For example, in FIGS. 4 and 5, the guide slots 236 bend in only one direction and therefore are suited for exposing the test sample to uni-directional bending. When the arms 216 are in the horizontal position shown in FIG. 4, the test sample is not subjected to any bending. As the arms 216 assume the pivoted position shown in FIG. 5, the test sample is subjected to bending in one direction. The arms 216 may be oscillated between the horizontal position and the pivoted position to subject the test sample to bending fatigue testing in one direction. Such testing may be suited for specific types of test samples, such as coronary artery stents, as the coronary artery is pre-disposed to uni-directional bending.

Figure 6:
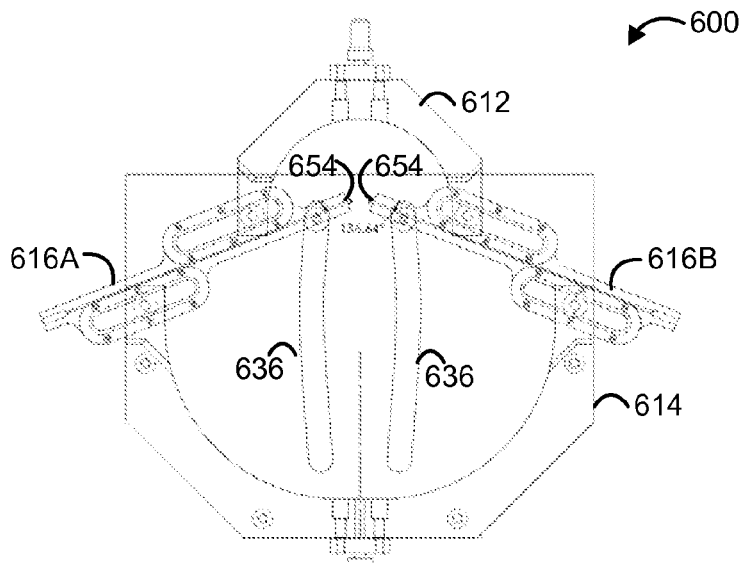
FIG. 6 is a plan view of another embodiment of a four-point bending fixture, illustrating the fixture with its arms in an upward pivoted position.
Figure 7:
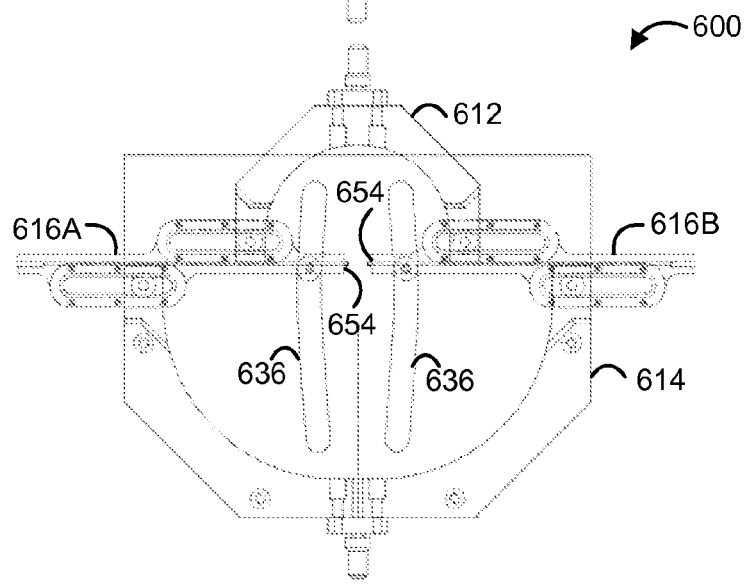
FIG. 7 is a plan view of the four-point bending fixture shown in FIG. 6, illustrating the fixture with its arms in a horizontal position.
Figure 8:
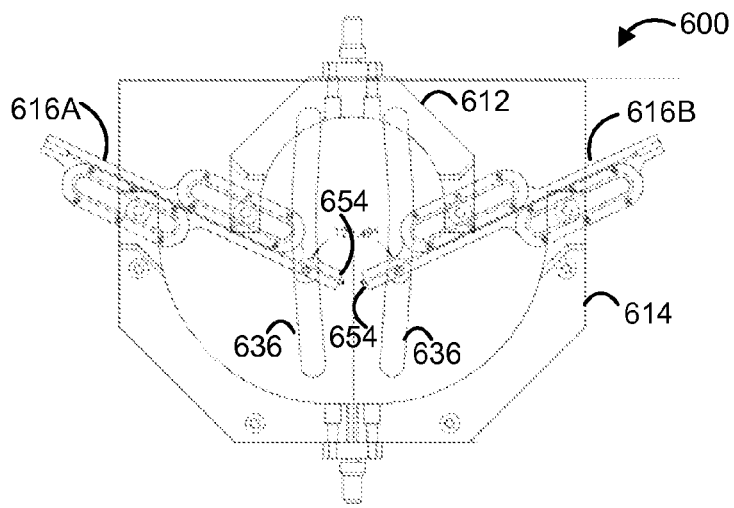
FIG. 8 is a plan view of the four-point bending fixture shown in FIG. 6, illustrating the fixture with its arms in a downward pivoted position.

As another example, in FIGS. 6-8, the guide slots 636 bend in two-directions and are suited for bi-directional bending. When the arms 616 are in the horizontal position shown in FIG. 7, the test sample is not subjected to any bending. As the arms 616 assume the upward pivoted position shown in FIG. 6, the test sample is subjected to bending in one direction. As the arms 616 assume the downward pivoted position shown in FIG. 8, the test sample is subjected to bending in the other direction. The arms 216 may be oscillated between the upward and downward pivoted positions to subject the test sample to bending fatigue testing in two directions.

Also as shown in FIGS. 6-8, the maximum angle of bending may be determined based on the angle formed between the inner end surfaces 654 of the arms 616 when the arms 616 have achieved a maximum pivot. When the arms 616 are in the maximum upward pivoted position, the inner end surfaces 654 form a maximum upward angle, and when the arms 616 are in the maximum downward pivoted position, the inner end surfaces 654 form a maximum downward angle. Because the arms 616 are relatively closer to the top of the slots 636 than the bottom of the slots 636 when the arms are in the horizontal position shown in FIG. 7, the arms 616 exhibit a smaller degree of rotation when in the maximum upward pivoted position, resulting in a smaller maximum upward angle, but the arms 616 exhibit a larger degree of rotation when in the maximum downward pivoted position, resulting in a larger maximum downward angle. Thus, the extent of the bending angle can be varied based on factors such as the initial position of the arm 616 in the slot 636, the length of the slot 636, and the extent to which the arm 616 traverse the slot 636.

From the above description, a variety of guide plates could be designed to achieve a variety of bending models, either alone or in combination with compression, tension, or some combination thereof.

In some embodiments, the fixture is configured to subject the test sample to bending in addition to torsion. The test sample is exposed to torsion by applying one or more torsional forces to one or more ends of the test sample. The torsional force may be applied in addition to the bending force, so that the torsional testing mode is superimposed on the bending testing mode. In particular, the torsional force is applied about an axis of rotation that lies in the plane of motion of the uni-axial test machine, such as parallel to a longitudinal axis of the arm.

The torsional force may be applied to the end of the test sample in a number of ways. In some embodiments, a cam surface may be positioned in the guide slot, and the arm may have an end portion that rotates upon encountering the cam surface, applying a torsional load on the sample. In such embodiments, the extent of torsion can be varied by varying the shape of the cam surface in the guide slot, and the timing of the torsion can be varied by varying the placement of the cam surface in the guide slot. The cam surfaces also may be interchangeable, so that the torsional force can be varied.

Figure 9:
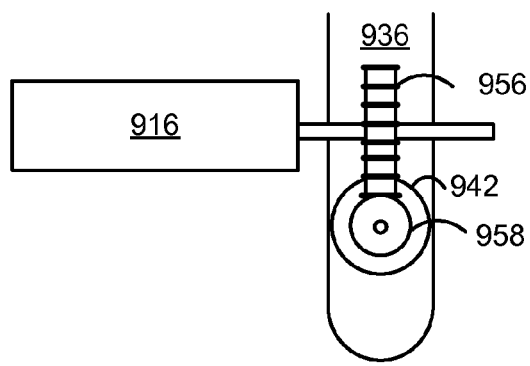
FIG. 9 is a front plan view of a system for exposing a testing sample to a torsional load.
Figure 10:
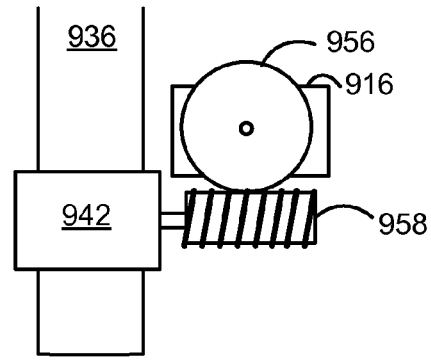
FIG. 10 is a side plan view of the system shown in FIG. 9.

Another embodiment of a system 900 for exposing the test sample to torsion is shown in FIGS. 9 and 10, wherein FIG. 9 view is a front plan view and FIG. 10 is a side plan view of a the system 900. A gear 956 is mounted to the end of the arm 916, the gear 956 having an axis of rotation that is parallel to the longitudinal axis of the arm 916. The test sample is mounted to the axis of rotation of the gear 956. The gear 956 engages a worm gear 958 that is mounted to the roller 942 in the guide slot 936, the worm gear 958 sharing an axis of rotation with the roller 942. As the roller 942 rotates in the guide slot 936, the worm gear 958 rotates about it axis of rotation, causing the corresponding gear 956 to rotate, applying a torsional force to the test sample. In such embodiments, the gears 956, 958 can be substituted with gears having various ratios to vary the torsional force applied to the test sample. Additionally, one or both of the gears 956, 958 can be removed so that a torsional load is not applied to the test sample. Torsion may be conducted alone or in combination with other testing modes, such as bending, bending and compression, or bending and tension.

Also in some embodiments, the fixture is configured to subject the test sample to radial pulsation. An example of such an embodiment is described with reference to FIG. 1. In particular, the fixture 200 is in communication with a fluid pump 160 via a fluid supply line 162 and a fluid return line 164. An enclosure, such as a sleeve, is positioned about the test sample between the inner ends of the arms, forming a fluid tight connection so that a flow of fluid can traverse the gap between the anus. In some embodiments, the enclosure is specifically designed to model the environment in which the test sample will be used. For example, in cases in which the test sample is a stent, the enclosure may model the intended implantation site for the stent, such as an artery.

The supply line 162 may supply a flow of fluid to the enclosure, and the return line 164 may return the flow of fluid from the enclosure. For example, as shown in FIG. 1 the supply line 162 may be associated with the outer end of the right arm, and the return line 164 may be associated with the outer end of the left arm. Each arm may define a longitudinal channel for communicating a flow of fluid between the two ends of the arm. Examples of longitudinal channels within the arms are shown in FIG. 3. In such embodiments, a closed fluid path is defined between the fluid pump, the supply line 162, the longitudinal channel of one arm, the enclosure about the test sample, the longitudinal channel of the other arm, and the return line 164. However, the closed fluid path may be formed in other manners.

In use, the fluid pump 160 is operated to drive fluid along the fluid path. The pump 160 may be operated in a pulsatile manner, so that the test sample is exposed to radially outwardly directed forces in a pulsatile manner. In some embodiments, the pump 160 is controlled by a computer system 166, described in further detail below. Radial pulsation may be conducted alone or in combination with other testing modes, such as bending, compression, tension, and torsion.

In embodiments, the fluid may be heated to mimic the conditions within the human body. The heated fluid may directed through the fluid circuit in a pulsatile manner to effectuate radial pulsation, or in a continuous manner to replicate the conditions in the body Without radial pulsation. The fluid may include water; a physiological fluid, such as blood; or a synthetic composition that mimics one or more properties (e.g., viscosity) of a physiological fluid.

In embodiments configured for radial pulsation, an uninterrupted fluid path may be formed from one arm through the test sample and out of the other arm, defining a closed fluid circuit. Thus, any structures intervening between the arm and the test sample may have a channel that permits fluid flow. For example, a channel may be formed within any sample holders, such as is shown in FIG. 3. Additionally, a channel may be formed through the shaft of a gear mounted to the end of the arm for the purpose of imparting torsion on the sample, such as a gear of the type shown in FIG. 9.

As mentioned above, the test system 100 may include a computer system 166 in some embodiments. The computer system 166 may be a general purpose or special purpose computer. The computer system 166 includes a memory that stores a mechanical testing module, such as a program designed to perform a mechanical testing analysis of a test sample. The computer system 166 also includes a processor that executes the mechanical testing module, such as to perform the mechanical testing analysis for the test sample.

One or more inputs may be provided to the computer system 166, either manually or electronically. Potential inputs include information about the uni-axial test machine, such as the position of the crosshead, the load applied to the fixture, the starling and final positions of the crosshead, and the rate of oscillation of the crosshead; information about the fixture, such as its inertia, the configuration of guide slots in the guide plate, and the starting and final positions of the arms; information about the sample, such as its size and materials of formation; and information about the bending mode, such as whether the sample is being exposed to bending alone or in combination with compression, tension, torsion, and radial pulsation. Upon execution by the processor, the mechanical testing module may perform a mechanical testing analysis of the test sample based on one or more of the input conditions.

In embodiments, the computer system 166 also may act as a controller for one or more of the components within the system. For example, the computer system 166 may control aspects of the uni-axial test machine, such as its starting position and rate of oscillation. The computer system 166 also may control the fluid pump 168. A person of skill will appreciate that the term "computer system" generally refers to one or more computing components intended to perform the operations or functions described above.

The computer system 166 also may receive information from a load cell 168 associated with the crosshead 106. The load ceil 168 measures the linear force directed on the fixture

200 and outputs an appropriate signal. Although the output of the load cell 168 is reported to the computer system 166 in the illustrated embodiment, the output may be reported to a display that is read by a human operator in other embodiments, or the load cell 168 may be omitted completely.

In embodiments, some or all of the fixture may be formed from materials that are lightweight, corrosion resistant, or some combination thereof. One example of a suitable material is a polyoxymethylene plastic material, such as a Delrin® brand material available from E. I du Pont de Nemours and Company. Forming the fixture from lightweight materials may facilitate decreasing the inertia of the fixture, so that a more sensitive load cell can be used. Forming the fixture from corrosion-resistance materials may facilitate submerging the fixture in a heated physiologic bath. However, other materials may be used for all or part of the fixture.

In some embodiments, the fixture may be configured to stabilize the movement of the arms in the plane of motion. For example, tire arms may be positioned on or between one or more stabilizing rollers, which may reduce movement of the arms out of the plane of motion. Such stabilization may be particularly helpful during high-speed fatigue testing.

In some embodiments, the system may be designed to detect a fracture in the test sample. A closed electrical circuit may be formed between the test sample, two electrical leads, and an appropriate monitoring device. When the test sample experiences a fracture, tire electrical circuit may experience a detectable change that is detected by the monitoring device. For example the monitoring device may be a multimeter or a milliohmmeter that can detect a change in electrical resistance across the leads.

In some embodiments, the monitoring device is mounted to the uni-axial test machine, such as on its crosshead. The monitoring device may be in electrical communication with a computer system, such as the computer system 166 described above. The computer system receives information about the electrical resistance of the circuit and process this information to identify a fracture in the test sample.

In some embodiments, the electrical leads are attached to opposite ends of the test sample. In other embodiments, the electrical leads are attached to sample holders, such as sample holders 344 shown in FIG. 3, which in turn are attached to the test sample. The sample holders 344 may be formed of a metallic material such as brass, so that the sample holders 344 serve as electrical points of contact for the electrical leads. The closed electrical circuit is defined by the test sample, the sample holders, and the leads in such embodiments.

The dimensions of the fixture can be sized to accommodate test samples of various dimensions. For example, the arms may be sized to accommodate test samples having a range of lengths and diameters. The distance between the prongs on the upper and lower links may vary, or the overall size of the fixture may vary, in some embodiments, the fixture also may be adjustable to accommodate test samples of various sizes. For example, the guide plate may be split vertically along its entire height into two half plates, each of which are adjustably mounted to the fixture so that the position of the guide slots can be adjusted by adjusting the relative position of the two half plates. Additionally, the upper and lower connecting links can be slit vertically into two half links, each of which is adjustably mounted to the test machine, so that arms can be moved closer together or farther apart to accommodate test samples of various sizes.

In embodiments, the systems and methods described herein can be used in mechanical tests that are conducted under conditions that replicate physiologic conditions within the body. For example, the mechanical tests may be carried out within a heated bath or oven. As another example, the radial pulsation system may be operated with a heated fluid flowing through its chamber and the pump disabled.

Figure 11:
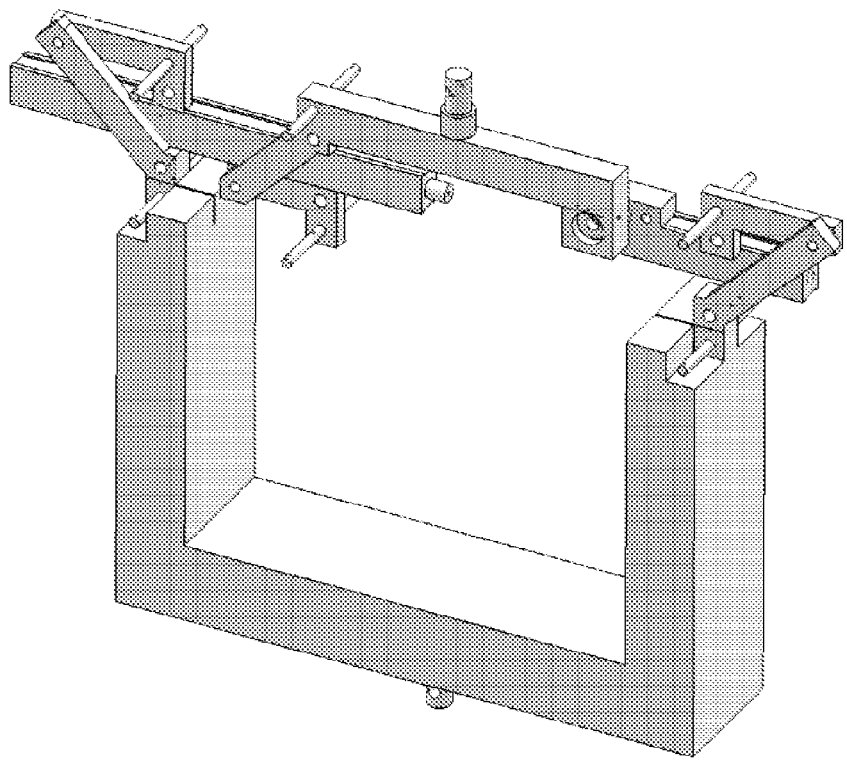
FIG. 11 is a perspective view of another embodiment of a four-point bending fixture.

FIG. 11 is a perspective view of another embodiment of a fixture 1100. Articulation of the upper and lower components with the arms is achieved through the use of ball bearings, from above and below, fixed by inner diameter pins. Upper and lower support of the arms allows for control over positive or upward aid negative or downward bending displacement. Initial tension between roller contacts, to maintain contact with the arms and/or support the weight of the roller, is provided by extension springs, located on either side of the roller bearing (not shown). Structural coupling between roller bearings is provided by two connecting members, joined by a sleeve bearing. One side of the upper component and corresponding arm are pinned, through one or more ball bearings affixed in the upper component. Pinning allows for precise, repeatable sample alignment and assists with positive and negative bending displacement. Tension and/or compression can be imparted by constraining insertion rod translation, for example, by increasing the spring tension securing the rolling contacts on the free (un-pinned) end of the apparatus. In some embodiments, one or more of the ball bearings, pins, extension springs, and sleeve bearings may be corrosion-resistant.

Within the present disclosure, directional terms such as upper, lower, left, right forward, rearward, vertical, and horizontal assume a test machine that is level to the ground and a fixture that is level within the test machine. These directional terms are employed for ease of reference and may or may not limit the disclosure, depending on the context. A person of skill will appreciate whether tire described components may have other directions, orientations, or positions depending on actual operational conditions.

Methods of subjecting a test sample to mechanical tests also are disclosed herein. The methods enable using a linear force to expose a test sample to bending forces. In particular, a test sample may be attached to two pivot arms such that tire test sample is suspended between the arms. The pivot arms may be capable of pivoting in a plane of motion. The method includes receiving a linear force and dividing the linear force into two smaller linear forces. Both of the smaller linear forces may have lines of action within the plane of motion, the lines of action parallel to but spaced apart from each other. One of the smaller linear forces may be directed onto one of the pivot arms and the other of the smaller linear forces may be directed onto the other pivot arm. The application of the linear forces onto the pivot arms causes the arms to pivot in opposite directions in the plane of motion, one arm pivoting clockwise and the other arm pivoting counterclockwise. Thereby, the test sample may be exposed to bending forces.

As the arms pivot, a distance between ends of the arms can be controlled to control the application of compressive or tensile forces to the test sample. If the inner ends of the arms are spaced apart by a distance that ensures the sample is not compressed or stretched, the test sample is subjected to pure bending. If the inner ends of the arms are spaced farther apart, the test sample is exposed to bending and tension. If the arms are spaced closer together, tire test sample is exposed to bending and compression. The distance may be maintained as the arms pivot so that the test sample is subjected to a single test mode over the entire range of motion, such as pure bending, bending and compression, or bending aid tension. The distance between the ends of the arms also may be varied as the arms pivot, varying the test mode between bending alone or in combination with compression and tension. Controlling the distance between the inner ends of the arms as the arms pivots ensures the test sample is subjected to the selected testing mode. For example, the distance between the inner ends of the arms may be controlled by constraining the arms to travel along a selected path, such as by movably fixing a portion of the arm in a guide slot.

A range of pivot of the arms can be controlled to control a maximum bending angle to which the test sample is exposed. For example, the arms may be rotated through a bigger angle of rotation to subject the test sample to a bigger maximum bending angle, or the arms may be rotated through a smaller angle of rotation to subject the test sample to a smaller maximum bending angle.

A range of pivot of the arms also can be controlled to control whether the test sample is exposed to uni-directional or bi-directional bending. For example, to subject the test sample to bending in only one direction, the arms may rotate away from a horizontal or rest position in a single direction and may return to the horizontal or rest position without passing it. To subject the test sample to bending in two directions, the arms may rotate away from a horizontal or rest position in one direction and may return to the horizontal or rest position before rotating away from the horizontal or rest position in the other direction.

The arms may be pivoted in an oscillating fashion to subject the test sample to fatigue testing. For example, the arms may be oscillated by reversing the direction of the linear force in an alternating fashion. The speed at which the force is reversed may determine the rate of oscillation used for the fatigue testing.

One or both ends of the test sample may be rotated to expose the test sample to torsional forces. For example, the test sample may be rotated about a shaft extending from an end of at least one of the arms, the shaft rotating about an axis of rotation that is generally coincident with a longitudinal axis of the at least one arm.

Fluid also can be flowed along a closed fluid path between the arms in a pulsatile manner to expose the test sample to radially pulsating forces. Thus, the test sample can be subjected to bending forces along with one or more compressive forces, tensile forces, torsional forces, or radially pulsating forces.

While particular embodiments have been disclosed in the present description and figures for purposes of example, those skilled in the art will understand that variations and modifications may be made without departing from the scope of the disclosure. For instance, features that are illustrated or described with reference to one embodiment, may be used on another embodiment to yield yet another embodiment. All such variations and modifications are intended to be included within the scope of the present disclosure, as protected by the following claims and the equivalents thereof.

We claim:

1. A fixture for subjecting a test sample to bending forces using a uni-axial test machine that applies a linear force, the uni-axial test machine comprising a frame and a crosshead that translates with reference to the frame in a plane of motion to generate the linear force, the fixture comprising:
   an upper connecting link configured to attach to the crosshead of the uni-axial test machine for receiving the linear force, wherein the upper link comprises two downwardly extending upper prongs, including a left upper prong and a right upper prong, each upper prong associated with an upper roller, the left upper prong associated with a left upper roller and the right upper prong associated with a right upper roller;
   a lower connecting link configured to attach to the frame of the uni-axial test machine, wherein the lower link comprises two upwardly extending lower prongs, including a left lower prong and a right lower prong, each lower prong associated with a lower roller, the left lower prong associated with a left lower roller and the right lower prong associated with a right lower roller; and
   two transverse arms pivotably carried between the upper and lower connecting links, each transverse arm having an inner end that is configured to attach to the test sample so that the test sample is suspended between the arms, the transverse arms operable to pivot in opposite directions in response to the linear force applied to the upper connecting link, exposing the test sample to bending forces, wherein each of the transverse arms is pivotably carried between the upper and lower links on one of the upper rollers and one of the lower rollers, a left transverse arm carried on the left upper roller and the left lower roller, and a right transverse arm carried on the right upper roller and the right lower roller.

2. The fixture of claim 1, wherein:
   the upper connecting link, the lower connecting link, and the transverse arms lay in the plane of motion;
   the fixture further comprises a guide plate laying in a plane that is parallel to but spaced apart from the plane of motion, the guide plate having two guide slots; and
   the transverse arms are movably guided along the guide slots to control a distance between the inner ends of the transverse arms.

3. The fixture of claim 2, wherein the guide plate can be substituted with another guide plate having different guide slots, the different guide slots causing the inner ends of the transverse arms to be closer together or farther apart so that the test sample is subjected to compressive or tensile forces.

4. The fixture of claim 2, wherein the guide plate can be adjusted to adjust the spacing of the guide slots, causing the inner ends of the transverse arms to be closer together or farther apart so that the test sample is subjected to compressive or tensile forces.

5. The fixture of claim 1, wherein at least one of the transverse arms is associated with a gear system operable to apply a torsional force to the test sample.

6. The fixture of claim 1, further comprising an enclosure that creates a closed fluid path between the transverse arms, wherein each of the transverse arms comprises an inner channel for providing fluid to or returning fluid from the sleeve.

7. A test system comprising:
   a frame;
   a crosshead that is operable to translate up and down within the frame;
   a lower link that is fixably mounted to the frame;
   an upper link that is fixably mounted to the crosshead; and
   two arms that are pivotably mounted between the upper and lower links, the arms operable to pivot in opposite directions in response to translation of the crosshead, wherein a closed fluid path is formed between the two arms, the closed fluid path in fluid communication with a pump that is operable to direct fluid through the closed fluid path in a pulsatile manner.

8. The test system of claim 7, further comprising a guide plate having two guide slots, wherein the arms are movably guided along the guide slots to control a distance between ends of the arms.

9. The test system of claim 8, wherein the guide plate can be adjusted or substituted to change the configuration of the guide slots, changing the distance between the ends of the arms.

10. A method of using a linear force to expose a test sample to bending forces, the method comprising:

attaching the test sample to two pivot arms such that the test sample is suspended between the arms;

transferring a linear force onto each of the pivot arms such that the arms pivot in opposite directions, exposing the test sample to bending forces; and flowing fluid in a pulsatile manner through a closed fluid path between the arms to expose the test sample to radially pulsating forces.

11. The method of claim 10, further comprising controlling a distance between ends of the arms to control the application of compressive or tensile forces to the test sample.

12. The method of claim 10, further comprising varying a distance between ends of the arms to vary the application of compressive or tensile forces to the test sample.

13. The method of claim 10, further comprising controlling a range of pivot of the arms to control a maximum bending angle to which the test sample is exposed.

14. The method of claim 10, further comprising reversing the direction of the linear force to subject the test sample to fatigue testing.

15. The method of claim 10, further comprising causing a shaft extending from an end of at least one of the arms to rotate about an axis of rotation that is generally coincident with a longitudinal axis of the at least one arm, exposing the test sample to a torsional force.

16. The method of claim 10, wherein the linear force is transferred to the pivot arms through a connecting link, the connecting link comprising an upper connector and two lower prongs, the lower prongs being spaced apart from each other in a symmetrical manner with reference to the upper connector, each of the lower prongs associated with one of the pivot arms, the upper connector receiving the linear force and each lower prong transferring a portion of the linear force onto one of the pivot arms.

17. The method of claim 10, wherein ends of the pivot arms are constrained in guide slots, such that application of the portion of the linear force to the pivot arms causes the ends of the arms to travel along the guide slots.

18. The method of claim 10, wherein the test sample is a medical stent or another implantable medical device.

* * * * *